(12) United States Patent
Tooley et al.

(10) Patent No.: US 8,191,868 B2
(45) Date of Patent: Jun. 5, 2012

(54) FLOATING OXYGENATION CIRCULATOR PLATFORM (OCP) WITH SUB-VORTEX INDUCTION MEANS

(76) Inventors: William Frederick Tooley, Platte, SD (US); Thomas Jerome Tooley, Clintonville, WI (US)

(*) Notice: Subject to any disclaimer, the term of this patent is extended or adjusted under 35 U.S.C. 154(b) by 762 days.

(21) Appl. No.: 12/251,372

(22) Filed: Oct. 14, 2008

(65) Prior Publication Data

US 2010/0093074 A1    Apr. 15, 2010

(51) Int. Cl.
*B01F 3/04*    (2006.01)
(52) U.S. Cl. .......................... 261/91; 261/120
(58) Field of Classification Search .............. 261/91, 261/120; 210/242.2
See application file for complete search history.

(56) References Cited

U.S. PATENT DOCUMENTS

| | | | | |
|---|---|---|---|---|
| 2,346,366 A * | 4/1944 | Durdin | ........................ | 366/265 |
| 3,680,845 A * | 8/1972 | Carlsmith et al. | .............. | 261/37 |
| 3,735,926 A * | 5/1973 | Ravitts | .............................. | 239/16 |
| 3,797,809 A * | 3/1974 | Sydnor, Jr. | ....................... | 261/91 |
| 3,827,679 A * | 8/1974 | Kaelin | .............................. | 261/91 |
| 3,846,516 A * | 11/1974 | Carlson | ............................ | 261/87 |
| 3,865,721 A * | 2/1975 | Kaelin | ........................... | 210/627 |
| 4,465,645 A * | 8/1984 | Kaelin | .............................. | 261/87 |
| 6,241,221 B1 * | 6/2001 | Wegner et al. | ................... | 261/93 |
| 7,267,328 B2 * | 9/2007 | Witheridge | ....................... | 261/77 |
| 7,789,553 B2 * | 9/2010 | Tormaschy et al. | ............ | 366/262 |
| 2007/0200261 A1 * | 8/2007 | Hills | ............................... | 261/84 |

* cited by examiner

Primary Examiner — Charles Bushey

(57) ABSTRACT

A floating oxygenation circulator platform (OCP) is disclosed employing sub-vortex induction to initiate numerous, gentle yet complex, tumbling, swirling, rolling, roiling or rotating sub-vortices spreading outward on the liquid surface. The circulator platform itself sets in motion a non-turbulent, high efficiency, bottom to top, primary toroidal vortex flow. Varied sub-vortex induction mechanisms mounted on, made part of, attached to, extending out from or placed around the body of the circulator platform, induce sub-vortices to increase the surface exposure of the liquid and its contents to atmospheric oxygen and UV sunlight. The OCP and its sub-vortex induction mechanisms taken together act in the manner of a Rotating Inverse Biological Contactor (RIBC), labeled "inverse" because the liquid itself rotates and tumbles its contents into direct contact with the atmosphere and with sunlight, in contrast to RBC devices where solid disks rotate in and out of a liquid.

5 Claims, 1 Drawing Sheet

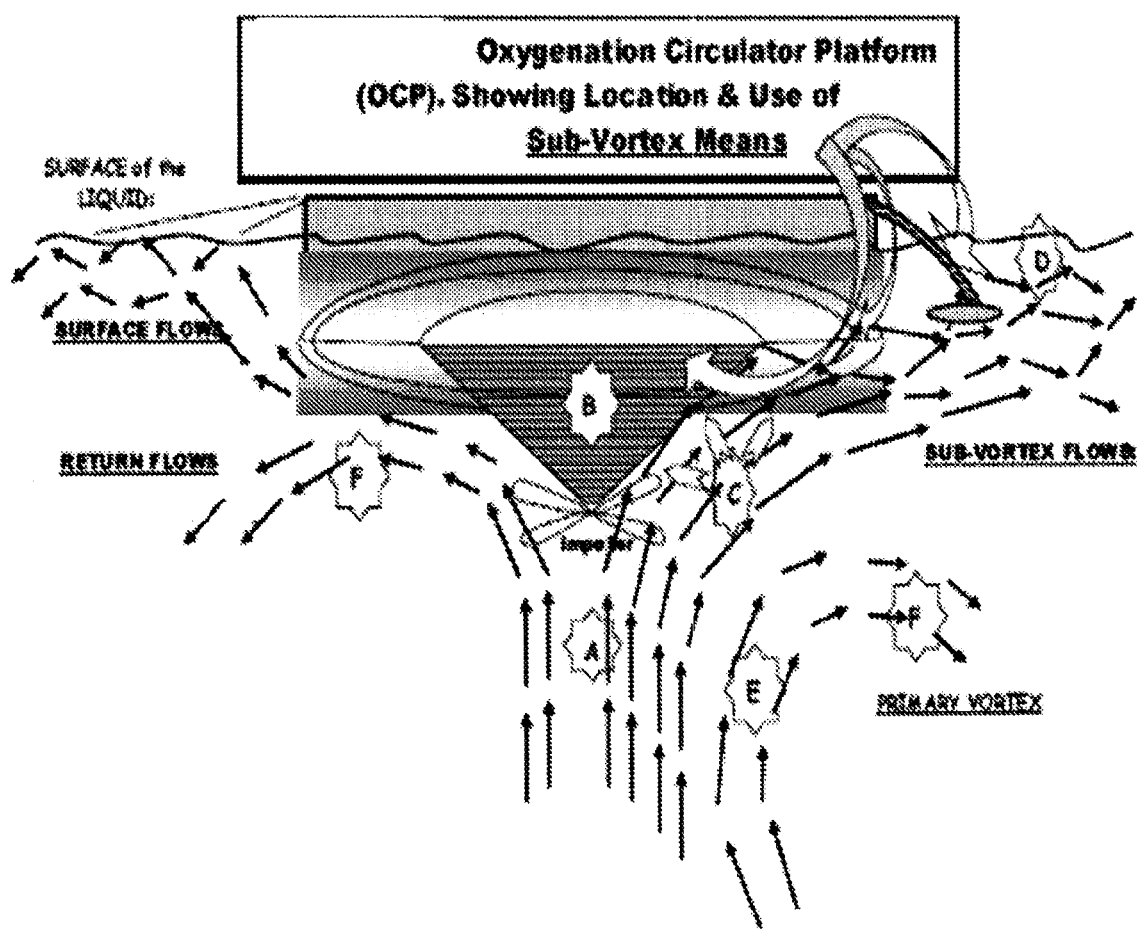

FLOATING OXYGENATION CIRCULATOR PLATFORM (OCP) WITH SUB-VORTEX INDUCTION MEANS

TECHNICAL HELD OF THE INVENTION

The present invention relates initially, and thus generally, to means that cause oxygenation and circulation in large liquid bodies and more specifically to processes intended to achieve high rates of re-oxygenation, microbial digestion, BOD reduction, nutrient stabilization as well as high rates of pathogen inactivation and large molecule degradation from exposure to UV radiation from sunlight striking the surface of a liquid body. Devices to accomplish any or all of these tasks are commonly referred to as paddlewheels, pumps, pond mills, circulators, stirrers, mixers, air compressors, bubble blowers, bubble diffusers and the like—indeed anything that causes circulation in a liquid body.

The present invention is built on a floating oxygenation circulator platform (OCP), having a submerged impeller designed specifically to induce bottom-to-top toroidal flow in large liquid bodies by lifting water to the surface. More specifically, the present invention sets forth varied apparatus which, in combination with the action of the circulator platform, induce and initiate sub-vortex formations on the surface of the liquid to increase exposure of the liquid and its contents to oxygen and sunlight.

Because the invention acts to induce the formation of complex sub-vortex flows at the surface of the liquid moving outward from the platform, the disclosed circulator platform supports enhanced oxygen transfer and re-oxygenation and can be used wherever increased DO and reduced BOD are desired as in water remediation and water quality improvement in natural lakes and ponds, water reservoirs, stock dams, drinking water impoundments, storm water detention ponds, human waste and sewage treatment ponds, manure transformation ponds and nutrient waste treatment ponds, industrial waste treatment facilities and the like.

Because the device increases exposure of liquid contents to UV sunlight by gently tumbling, swirling, rotating rolling or roiling the surface of the liquid repeatedly, exposing the liquid contents to UV radiation at the surface the devise will be useful wherever the intention is to inactivate pathogens and degrade large molecules.

Due the to rotating and tumbling action of numerous, complex sub-vortices formed at the surface, the invention acts as a Rotating Inverse Biological Contactor intended to move nutrients and microbes in and out of direct contact with atmospheric oxygen and sunlight. Furthermore, return flows from the surface drag algae and other surface colonizing organisms down into the liquid where sunlight is less available. Water movement disturbs the ability of such organisms to colonize on the surface and lack of sunlight limits their ability to bloom. This returns advantage to competing aquatic organisms and helps to re-establish balance in aquatic ecosystems. Finally circulation transports dissolved oxygen down to the sediment layer reducing sludge deposits where exotic weeds such as milfoil take root and flourish. Reduction of sludge and sediment where milfoil and other exotic weeds take root can quickly reduce their dominance in bays, lakes, estuaries and reservoirs and is a specific intended use for this apparatus.

BACKGROUND AND PRIOR ART

While other aerator-circulators claim to move liquid to the surface, either by accident or by design, and some mechanisms may attempt to enhance surface area and exposure by violent surface disruption including heaters, blowers, pulsaters, frothers, wave machines, and other mechanical means, there has been no attempt to increase the surface exposure of the contents of a liquid body to atmospheric oxygen and UV radiation by mechanisms intended for inducing numerous and complex, surface sub-vortices that provide gentle swirling, rolling, roiling, rotating or tumbling while avoiding turbulence, maintaining a complex, quiescent, non-violent flow and thereby avoiding unintended disruption to fragile microbial digestion, reproduction as well as bio-floc or bio-film forming processes.

The present invention improves the performance of conventional wastewater treatment ponds and water remediation activities by adding means to generate numerous complex sub-vortices in liquid flows on a quiescent surface and to increase liquid re-oxygenation, as well as exposure of liquid contents to UV sunlight. The apparatus brings microbes and nutrients together and into contact with each other and with atmospheric and dissolved oxygen. Likewise the apparatus aids pathogen inactivation and large molecule degradation by bringing liquid contents into increased exposure to UV radiation from sunlight.

The floating oxygenation circulator platform (OCP), designed in accordance with the present invention represents a variety of improvements to existing technology that are specifically designed to induce gentle, non-disruptive sub-vortices in a liquid flow, thus to increase and enhance the exposure of liquid contents to atmospheric oxygen and UV sunlight radiation at the surface during circulation and to enhance microbial digestion by bringing microbes and nutrients together, in contact with oxygen while avoiding violent disruption.

It is contemplated that the present invention relates to a variety of different fields. Initially, it is thought that the invention applies to fields which include, but are not limited to, any floating, suspended, fixed or mounted apparatus for circulation in liquids including stirrers, bubble blowers, compressors, pumps, pond mills and other apparatus claimed to mix or circulate liquid. The present invention relates most directly to devices for creating bottom to top circulation and mixing in large liquid bodies, usually greater than one million gallons and typically in bodies of 10 million to 100 million gallons or larger without limit.

Limitations of Other Oxygenation Devices and Other Circulators.

Traditionally with regard to the oxygenation of liquids, bubble blowers and air diffusers linked to pumps and compressors have been used to inject air under pressure into liquid bodies in an attempt to oxygenate the liquid and satisfy oxygen demand. It has been thought that the more air injected, the greater the pressure applied and the smaller the bubbles, the more oxygen would be imparted into the water. This path has led to systems that employ huge amounts of horsepower to force larger and larger quantities of air in smaller and smaller bubbles into a liquid. Experience has shown that such systems reach the limits of oxygen transfer at about 2-3 lbs of oxygen per horsepower. Over fifty years this experience has been instructive and has shown that above certain limits, increased horsepower with more violent disturbance to the liquid, produces decreasing amounts of microbial digestion for each increase in energy and effort.

How the Invention Addresses Technical Problems in Water and Wastewater Treatment and Remediation The invention described here as a floating oxygenation circulator platform (OCP), moves liquid to the surface using an impeller or other means to initiate upward flows. Moving liquid to the surface in this manner induces formation of a large, gentle, bottom-to-top toroidal vortex flow in the liquid body. Importantly the present invention combines this large toroidal vortex flow induction with means to induce gentle complex sub-vortices as liquid flows upward, around, past and out from the body of the circulator platform and moves outward on the surface of the liquid. The formation of gentle complex surface sub-vortices enhance microbial activity, contributes to large molecule degradation and supports pathogen inactivation in the following ways:

Surface sub-vortices expand the exposed surface to allow absorption of more atmospheric oxygen faster.

Complex surface sub-vortices enhance the exposure of pathogens and large molecules to direct UV sunlight for more effective pathogen inactivation and faster large molecule degradation.

Gentle surface sub-vortex activities tumble the microbial biomass into direct contact with atmospheric oxygen to increase biomass growth and vitality beyond the limits of dissolved oxygen alone.

Continuous circulation and gentle surface vortex activity brings colonies of microbes together into contact with nutrients, with oxygen and with each other to enhance the formation of numerous, complex bio-flocs and bio-films that can work together to accomplish complex microbial digestive tasks.

All this is accomplished without violent disruption to fragile microbial digestive activities or to the formation of delicate and complex bio-flocs and bio-films.

Sub-vortex induction means are mounted on, made part of, attached to, extended out from or placed around the circulator platform and arranged to induce or enhance sub-vortex formation on the surface of or deeper down in the liquid. The oxygenation circulator platform (OCP) with sub-vortex induction means produces a swirling, rolling roiling, rotating or tumbling in the liquid flow as it moves upward and outward past the body of the platform and across the surface of the liquid. These sub-vortices act to increase the surface exposure of liquid contents to atmospheric oxygen and UV sunlight. However no single means, structure, enhancement or embodiment of this invention, taken by itself, is likely to induce the desired sub-vortex flows and the desired exposure of fluid contents to oxygen and sunlight. It is only by combinations of sub-vortex induction means, enhancements or embodiments acting together or in sequence, that desired vortex flow patterns are induced in varied liquids with different flow kinetics and viscosities.

Therefore the present invention intends to patent a process utilizing an array of options to accomplish said process, without limiting the patent to any particular array or set of embodiments or options. The invention is in no way limited to any particular feature, embodiment or set of enhancements described herein, but makes claims that apply to any and all means that may be attached to, made part of, mounted on, extended from or placed around the body of a floating oxygenation circulator platform (OCP), and arranged for purposes of inducing gentle, complex sub-vortices in a fluid flowing upward and outward past the body of the platform. The invention claimed is embodied in the process of creating an enhanced primary vortex flow and induced complex sub-vortices in a liquid passing the body of a floating oxygenation circulator platform (OCP) by causing fluid to flow over, under, around or past any single or any variety of sub-vortex induction means mounted on, made part of, attached to, extended out from or placed around the circulator platform for the purpose of enhancing the exposure of liquid and its contents to oxygen and sunlight on a constantly renewing surface moving outward from the platform.

As with all rotating biological contactors (RBC's), aerobic digestion is enhanced when microbial organisms and colony forming units (CFU's) have direct and recurring contact with atmospheric oxygen. The primary advantages of the disclosed invention are therefore two fold:

Exposure of microbes and liquid contents to oxygen and sunlight on the surface of liquid is increased by the formation of numerous sub-vortices, formed in a gentle surface current without violent disturbance of microbial activity and with the result that more oxygen and UV radiation can be received by the liquid and its contents more quickly while avoiding disruption to quiescent microbial processes.

Since aerobic microbes brought into contact with the atmosphere breath oxygen directly, microbial digestion in liquids is no longer limited to or dependant solely upon the amount of oxygen that can be dissolved into the liquid.

The disclosed platform draws energy from an on-board solar array or from attached electrical lines. In natural settings, the low profile platform produces no audible noise, and offers little surface visibility or visual intrusiveness for onlookers enjoying the view.

The disclosed platform (OCP) is efficient and capable of bottom-to-top circulation, moving liquid in a range greater than 100,000 gallons per minute while expending less than one horsepower of energy. In toroidal circulation of this type, deep, wide and gentle liquid flow encourages microbial digestion by bringing nutrients and microbes together into contact with each other, and transporting them to the surface into contact with oxygen and UV sunlight. With the present invention, sub-vortices are initiated as the liquid passes in the vicinity of the device or is affected by contact with the body of the device or with contact with sub-vortex induction means mounted on, attached to, made part of, extended out from the device.

Induced sub-vortex surface action brings liquid contents more directly into contact with atmospheric oxygen and UV sunlight. At the expanded surface, the liquid itself absorbs dissolved oxygen to be re-distributed along with the nutrients and microbes throughout the liquid body. Gentle flows prevent violent disruption of quiescent microbial digestion and encourage formation of complex bio-floc and bio-film communities while avoiding disturbance of sediments and minimizing problematic re-suspension of solids. On the surface, repeated exposure of liquid contents to UV sunlight inactivates and destroys a wide range of disease pathogens that sicken animals and humans. UV sunlight also degrades dangerous large molecules, like dioxins and PCB's that can cause cancer. Finally complex sub-vortices in the top-downward return flow moves algae and other colonizing organism's and off the surface and out of the sunlight, thus reducing their capability to bloom and to block sunlight from competing aquatic life below. The present invention builds and improves upon prior circulation efforts by adding means to initiate and cause the formation of numerous complex, sub-vortex flows as liquid passes in the vicinity of the body of the OCP and moves outward from it.

BRIEF DESCRIPTION OF DRAWING

A clearer understanding of the present invention can be obtained by reference to a preferred embodiment set forth in the drawing that follows. Both the organization and method of operation of the invention may be more easily understood by reference to the illustration and subsequent descriptive statements. Although the illustrated embodiment is exemplary of a system for carrying out the present invention, the illustration is not intended to limit the scope of this invention, which is set forth with particularity in the claims as appended or as subsequently amended. The illustration is provided merely to clarify, make visible and exemplify the invention.

For a more complete understanding of the present invention, reference is now made to the elements of the drawing below:

FIG. 1: Artist's rendering of a floating, circulator platform with sub-vortex induction means in its general conceptual form;

FIG. 1-A: illustrates upward flows through the impeller

FIG. 1-B: illustrates optional friction reduction dimples and cups not unlike those on a golf ball;

FIG. 1-C: shows the direction of liquid pressure against the platform;

FIG. 1-D: illustrates the development of complex sub-vortex flows moving across the surface after contact with or passing in the vicinity of sub-vortex induction means;

FIG. 1-E: shows expansion of the main toroidal vortex flow along side upward flows initiated through the impeller.

FIG. 1-F shows return flows that draw algae and other colonizing organism off the surface and out of direct sunlight to prevent surface domination and bloom.

ILLUSTRATED OVERVIEW

Artist Rendering of a Floating Oxygenation Circulator Platform (OCP)

Large curved arrows point to areas of detailed patent claims showing where up-flows may contact the submerged body and out-flows may contact attached sub-vortex induction means extended out from the body of the platform. This illustration is not to scale and is not intended to elucidate the entire variety of means to induce complex sub-vortex formation—only the area of claims and the location of means.
Primary Vortex Main toroidal flow circulates millions of gallons of liquid per hour, bottom-to-top, bringing nutrients, and microbes together, and transporting dissolved oxygen throughout the liquid body.
Surface Flows Collect oxygen and enhance UV Exposure to inactivate pathogens and degrades large molecules.
Sub-Vortex Flows:

After contact with induction means mounted on, made part of, attached to or extended out from the platform.
Return Flows Draw off the surface to prevent colonization and bloom.

DETAILED DESCRIPTION OF PREFERRED EMBODIMENTS

As required, a detailed illustrative embodiment of the present invention is disclosed. Techniques, elements and operating structures in accordance with the present invention may be embodied in a wide variety of forms and manners, some of which may be quite different from those shown in this disclosed embodiment. Consequently, the specific structural and functional details disclosed herein are merely representative, yet in that regard, they are deemed to afford a good embodiment for purposes of disclosure and to provide a basis for the claims herein which define the scope of the present invention. The following presents a detailed description of a preferred embodiment as well as some alternative embodiments of the present invention.

Certain terminology may be used in the following description for convenience in reference only and will not be limiting. The words "in" and "out" will refer to directions in toward and out from, respectively, the geometric center of the device and designated and/or referenced parts thereof. The words "up" and "down" will indicate directions relative to the horizontal and as depicted in the various figures. The words "rotation—vertical and horizontal" will indicate movement around an axis. Terminology may include the words above specifically mentioned, derivatives thereof and words of similar import.

As mentioned above, the present invention includes a number of different forms, appearances, expressions, or enhancements to a floating circulator platform, which forms are intended to induce and create complex sub-vortices in the surface flows as liquid moves upward past and outward away from the circulator platform. Each of these means, can be combined with others in a variety of ways to achieve the desired goals of complex sub-vortices moving past and away from the circulator platform. It is the process of inducing complex sub-vortices in the flow by using features mounted on, made part of, attached to or placed around the body of the up-flow circulator platform as well as the myriad forms and expressions of said features that may be used to accomplish said outcomes, which are being patented.

The first step in the process induces an upward flow of liquid moving past the body of the circulator platform. This flow is initiated by any desired means, usually an impeller attached to or fixed below the platform. Initiating the up-flow is not part of the present patent claim, as it is merely a precursor to the present invention. Up flow circulators may already exist in other forms and embodiments.

This embodiment of the floating oxygenation circulator platform (OCP) is arranged so that the body of the platform extends downward into the liquid and outward across the surface in such a manner that liquid flows must move upward and push outward past the widening body of the platform, pushing against surrounding liquid and in turn being pushed back against the body of the platform by up-flow inertia as well as gravitational forces acting on the surround liquid. A floating platform arranged in such a manner that pressure from the surrounding liquid and up-flows moves liquid into intimate contact with varied sub-vortex induction means on the body of the platform is part of the disclosed invention and is a claim of the present patent.

On the submerged body of the platform, liquid encounters an array of dimples, cups, ridges, valleys, slots or other formations put there to interrupt and break-up laminar flows close to the body of the platform. This allows flows to move upward with reduced friction in unorganized flows so as not to impede the influence of sub-vortex induction means. Such varied means as protrusions, indentations, guidance vanes, fins, rudders, hydroplanes or other embodiments mounted on, made part of or attached to the body of the platform in ways intended to induce the formation of complex sub-vortices in the liquid flow are a claim of this patent.

After moving past the submerged portion of the platform body, flow continues outward and is brought into contact with any of the formations, mechanism, and devices mounted on, made part of the under-surface or attached to and extended outward from the body of the platform itself. Any means, mechanisms or embodiments designed to induce the formation of complex sub-vortices in the out-flow as it moves across the underside of the platform and moves out across the surface are a claim of this patent.

Upon reaching the surface, numerous complex sub-vortices spread outwards, pushed by liquid following behind. The movement of the liquid outward from the platform is not a claim of this patent. The means to induce the formation of complex sub-vortices in the surface flow is a claim of this patent.

Finally, while details have been disclosed, it is to be understood that this patent is not limited to the particular construction and arrangement of details shown, disclosed and illustrated herein. Rather the patent embraces all equivalent forms and embodiments thereof as described by and may fall within the scope of the claims.

We claim:

1. A floating oxygenation circulator platform (OCP), having a body for floatation, said body having a central vertical axis and a substantially submerged, outwardly facing surface and an impeller or other flow means arranged below the platform for generating bottom-to-top, highly efficient fluid-to-energy, toroidal vortex flows in liquid bodies which flow upwardly past and interact with said outwardly facing surface under the influence of said impeller or other flow means, and specifically having sub-vortex induction means mounted on, attached to, made part of, extending out from or placed around the outwardly facing surface of the body of said platform, said sub-vortex induction means arranged for generating numerous complex sub-vortices as liquid flows upward past the outwardly facing surface of the body of the circulator platform and spreads outward across the surface of the liquid.

2. A floating oxygenation circulator platform (OCP), including sub vortex induction means according to claim 1, with impeller or other flow means arranged below the platform so that liquid flows upward and outward under the platform in such a way that liquid flowing past the submerged portion of the body of the circulator platform, under pressure from forces of gravity and the inertia in the upward flow, makes contact with said sub-vortex means.

3. Sub-vortex induction means according to claim 2, comprising at least one of a group of varied elements, consisting of depressions, raised areas, dips, cups, bumps, dimples, ridges, valleys, slots, rings or other similar embodiments mounted on, made part of, attached to or extended out from the body of said oxygenation circulator platform (OCP), with said elements arranged and intended to initiate and influence development of numerous sub-vortices to induce gentle swirling, tumbling, roiling, rolling or rotating currents as liquid moves past the platform and outward onto the surface of the liquid.

4. Additional sub-vortex induction means according to claim 2, comprising at least one of a group of varied elements consisting of small fins, rudders, hydroplanes, rotational devices, vanes or other similar turbulence or guidance means mounted on, made part of, attached to, extended out from or placed around the perimeter of said oxygenation circulator platform (OCP) and extending down into the flowing liquid such that further sub-vortices are formed to produce gentle swirling, tumbling, roiling, rolling or rotating currents as well as up-welling and down-welling flows in the liquid moving past the body of the floating platform and outward away from the device.

5. A floating circulator platform according to claim 1 with sub-vortex induction means according to claims 3 or 4 wherein said platform and its sub-vortex induction means act together to function as a Rotating Inverse Biological Contactors (RIBC); acting as a rotating biological contactor (RBC) in that microbes and nutrients are transported into and out of direct contact with atmospheric oxygen and sunlight; and "inverse" in that the liquid itself is set into motion rather than any mechanical device rotating into and out of the liquid.

* * * * *